(12) United States Patent
Bristow

(10) Patent No.: US 9,617,247 B1
(45) Date of Patent: Apr. 11, 2017

(54) FORM OF HALOSULFURON-METHYL, A PROCESS FOR ITS PREPARATION AND USE OF THE SAME

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/955,385

(22) Filed: Dec. 1, 2015

(51) Int. Cl.
*A01N 47/36* (2006.01)
*A01N 25/12* (2006.01)
*A01N 25/14* (2006.01)
*C07D 403/12* (2006.01)

(52) U.S. Cl.
CPC .......... *C07D 403/12* (2013.01); *A01N 47/36* (2013.01)

(58) Field of Classification Search
CPC .................................................. A01N 47/36
See application file for complete search history.

(56) References Cited

U.S. PATENT DOCUMENTS

| | | | | |
|---|---|---|---|---|
| 4,263,440 A | * | 4/1981 | Handte | C07D 235/26 504/267 |
| 4,668,277 A | * | 5/1987 | Yamamoto | A01N 47/36 504/215 |
| 5,550,238 A | * | 8/1996 | Chiang | C07D 521/00 544/206 |
| 6,420,381 B1 | * | 7/2002 | Muraoka | C07D 471/04 514/300 |
| 2015/0031877 A1 | * | 1/2015 | Hiratsuka | A01N 43/84 544/105 |

OTHER PUBLICATIONS

HCAPLUS abstract 1999:261209 (1999).*
Roberts, R.M. et al. Modern Experimental Organic Chemistry. Holt, Rinehart and Winston, New York, 1979, pp. 49-58.*
Anonymous: '2.2 Recrystallization'. PDF [online], published online in Mar. 2011. [retrieved on Sep. 14, 2016]. Retrieved from the Internet:<URL: https://yvesrubin.files.wordpress.com/2011/03/recrystallization.pdf>.*
McClurg, R.B., "X-Ray Powder Diffraction (XRPD) to Describe Crystal Forms," Publication of SSCI an Aptuit Company, Jul. 9, 2008, pp. 1-23.*

* cited by examiner

*Primary Examiner* — John Pak
(74) *Attorney, Agent, or Firm* — Dickinson Wright PLLC

(57) ABSTRACT

The present invention describes the crystalline form of halosulfuron-methyl of formula (I), the crystal preparation process, the analyses of the crystal through various analytical methods and using the crystal to prepare stable agrochemical formulation. The invention also describes the use of various solvents towards the crystalline form preparation conditions.

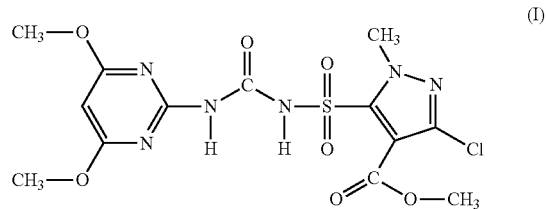

12 Claims, 4 Drawing Sheets

FORM OF HALOSULFURON-METHYL, A PROCESS FOR ITS PREPARATION AND USE OF THE SAME

BACKGROUND

Field

The present disclosure relates to a crystal form of methyl 3-chloro-5-(4,6-dimethoxypyrimidin-2-ylcarbamoylsulfamoyl)-1-methylpyrazole-4-carboxylate (halosulfuron-methyl), to its preparation processes and to its use in agrochemical preparations.

Description of Related Art

Halosulfuron-methyl (methyl 3-chloro-5-(4,6-dimethoxypyrimidin-2-ylcarbamoylsulfamoyl)-1-methylpyrazole-4-carboxylate) is from the sulfonylurea group of chemicals and used as herbicide. Halosulfuron-methyl has a wide herbicide activity spectrum for controlling weeds such as perennial grasses and broadleaf weeds either for pre or post emergence treatment. The active ingredient is absorbed by the root system and/or leaf surface of the weed species and works by inhibiting the AcetoLactate Synthase (ALS) enzyme which is responsible for the synthesis of proteins required for cell division and plant growth, and hence, the weeds will start discolor and die within few days after the treatment.

Halosulfuron-methyl has molecular formula of $C_{13}H_{15}ClN_6O_7S$. Its chemical structure is

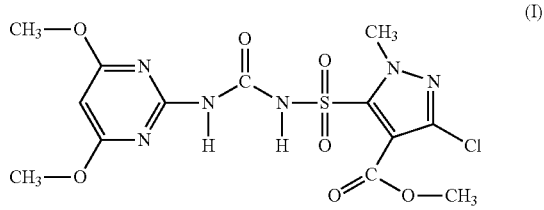 [SMILES: COC(=O)c1c(Cl)nn(C)c1S(=O)(=O)NC(=O)Nc1nc(OC)cc(OC)n1]

(I)

The commercially available halosulfuron-methyl, which is usually manufactured by the process described in U.S. Pat. No. 4,668,277, is present in an amorphous state. It has been found that halosulfuron-methyl in amorphous state is highly viscous, which is not suitable for being prepared as compositions or formulations having spray equipment cleanout property. Halosulfuron-methyl residues stay in the spray equipment after spraying. Adequate cleanout may require a rinsing procedure that is not only time-consuming but also results in wastewater disposal problem. Therefore, there is a need to provide a novel form of halosulfuron-methyl with increased solubility and decreased viscosity.

SUMMARY

Accordingly, an embodiment of the invention provides a novel crystalline form of halosulfuron-methyl, termed "crystalline modification I", and a process for its preparation as well as its use in agrochemical compositions. The novel crystalline modification I has been advantageously found to have increased solubility, decreased viscosity and improved spray equipment clean-out properties. Accordingly, an embodiment of the invention also provides compositions for controlling undesirable plant growth, such as weeds, comprising the crystalline modification I of halosulfuron-methyl on its own, as a mixture with auxiliaries and carriers, and as a mixture with other active compounds. The use of the crystalline modification I of halosulfuron-methyl in the control of undesirable plant growth and a method for the same are also provided by the invention.

DETAILED DESCRIPTION OF SPECIFIC EMBODIMENTS

It has been found that the present crystalline modification I of halosulfuron-methyl has a significant increase in its solubility and decrease in its viscosity, which significantly reduces the residue contamination and improve spray equipment clean-out properties. In addition, it is found that the crystalline modification I of halosulfuron-methyl is easier to be comminuted or ground compared to amorphous halosulfuron-methyl prepared in accordance with the disclosure of U.S. Pat. No. 4,668,277. This allows the preparation of commercial formulations such as suspension concentrates (SC), oil-based suspension concentrates (OD), water-dispersible granules (WG) and water-soluble granules (SG). Hence, it is possible to prepare any typically used herbicidal formulations of halosulfuron-methyl in crystalline modification I, which will be disclosed hereinafter.

By virtue of its high solubility and low viscosity, the crystalline modification I of halosulfuron-methyl is highly suitable for preparing compositions for controlling undesirable weeds.

According to the invention crystalline modification I of halosulfuron-methyl is provided, exhibiting at least 3 of the following reflexes as 2θ values in an X-ray powder diffractogram recorded using Cu—Kα radiation at 25° C.:

| | |
|---|---|
| 2θ=8.80±0.2 | (1) |
| 2θ=13.48±0.2 | (2) |
| 2θ=13.72±0.2 | (3) |
| 2θ=16.20±0.2 | (4) |
| 2θ=17.71±0.2 | (5) |
| 2θ=18.61±0.2 | (6) |
| 2θ=20.48±0.2 | (7) |
| 2θ=21.38±0.2 | (8) |
| 2θ=22.60±0.2 | (9) |
| 2θ=24.71±0.2 | (10) |
| 2θ=25.53±0.2 | (11) |
| 2θ=25.83±0.2 | (12) |

2θ=26.53±0.2 (13)

2θ=26.72±0.2 (14)

Figure 2:
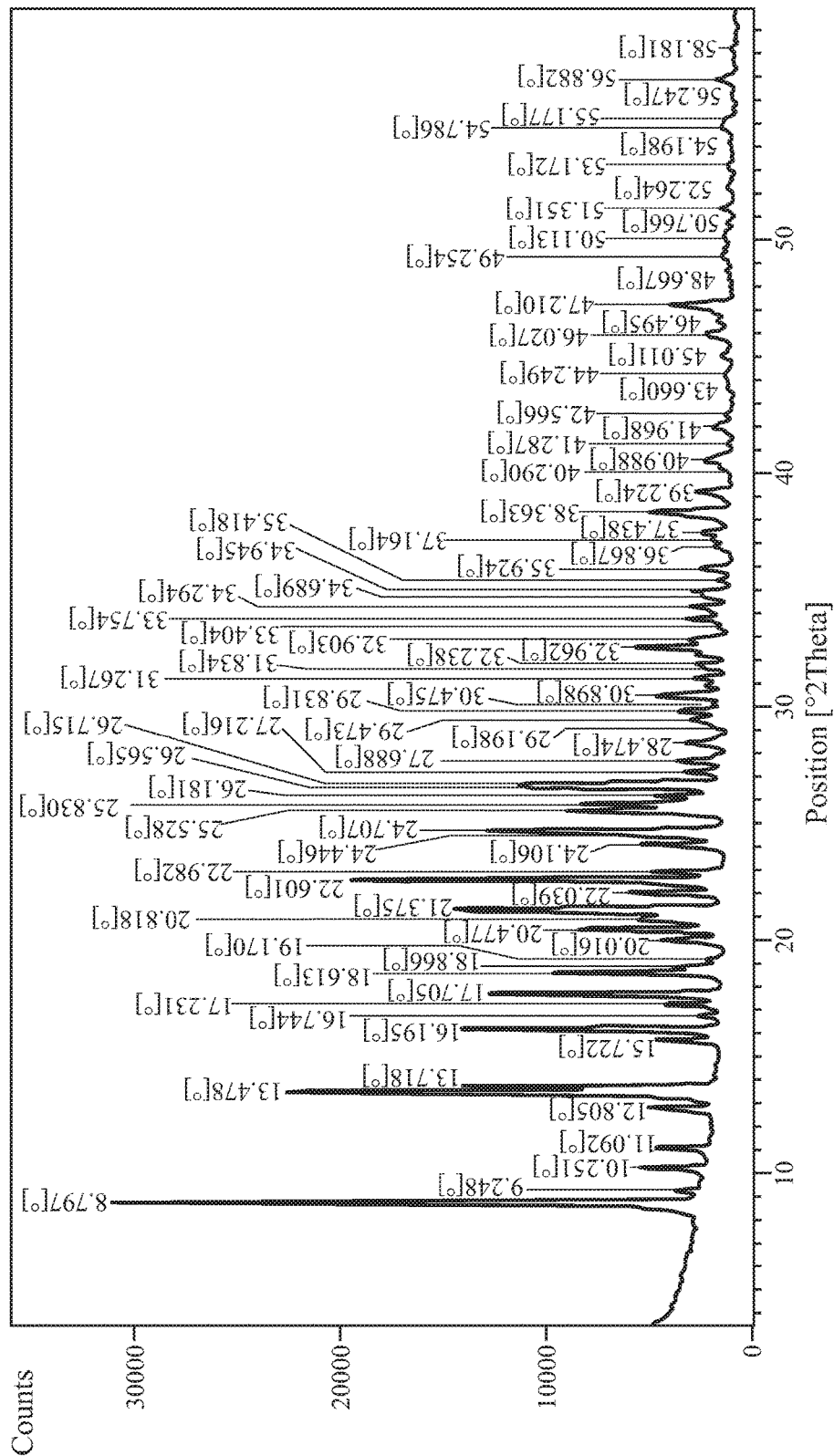
FIG. 2 is a graph showing the results of an X-ray powder diffractogram (XRD) of crystalline modification I of halosulfuron-methyl, according to an embodiment of the invention.

The crystalline modification I of halosulfuron-methyl of the invention is characterized by an X-ray powder diffractogram having at least three of the reflexes indicated above. Preferably, the crystalline modification I is one having at least four of the aforementioned reflexes, more preferably at least five, six, or seven, or eight of said reflexes. An X-ray powder diffractogram of the crystalline modification I of halosulfuron-methyl is shown in FIG. 2, which will be described in detail hereinafter.

According to a preferred embodiment the crystalline modification I exhibits at least 3, 4, or 5 or all of the reflexes from the following:

2θ=8.80±0.2 (1)

2θ=13.48±0.2 (2)

2θ=13.72±0.2 (3)

2θ=16.20±0.2 (4)

2θ=17.71±0.2 (5)

2θ=21.38±0.2 (8)

2θ=22.60±0.2 (9)

2θ=24.71±0.2 (10)

2θ=26.72±0.2 (14)

Figure 1:
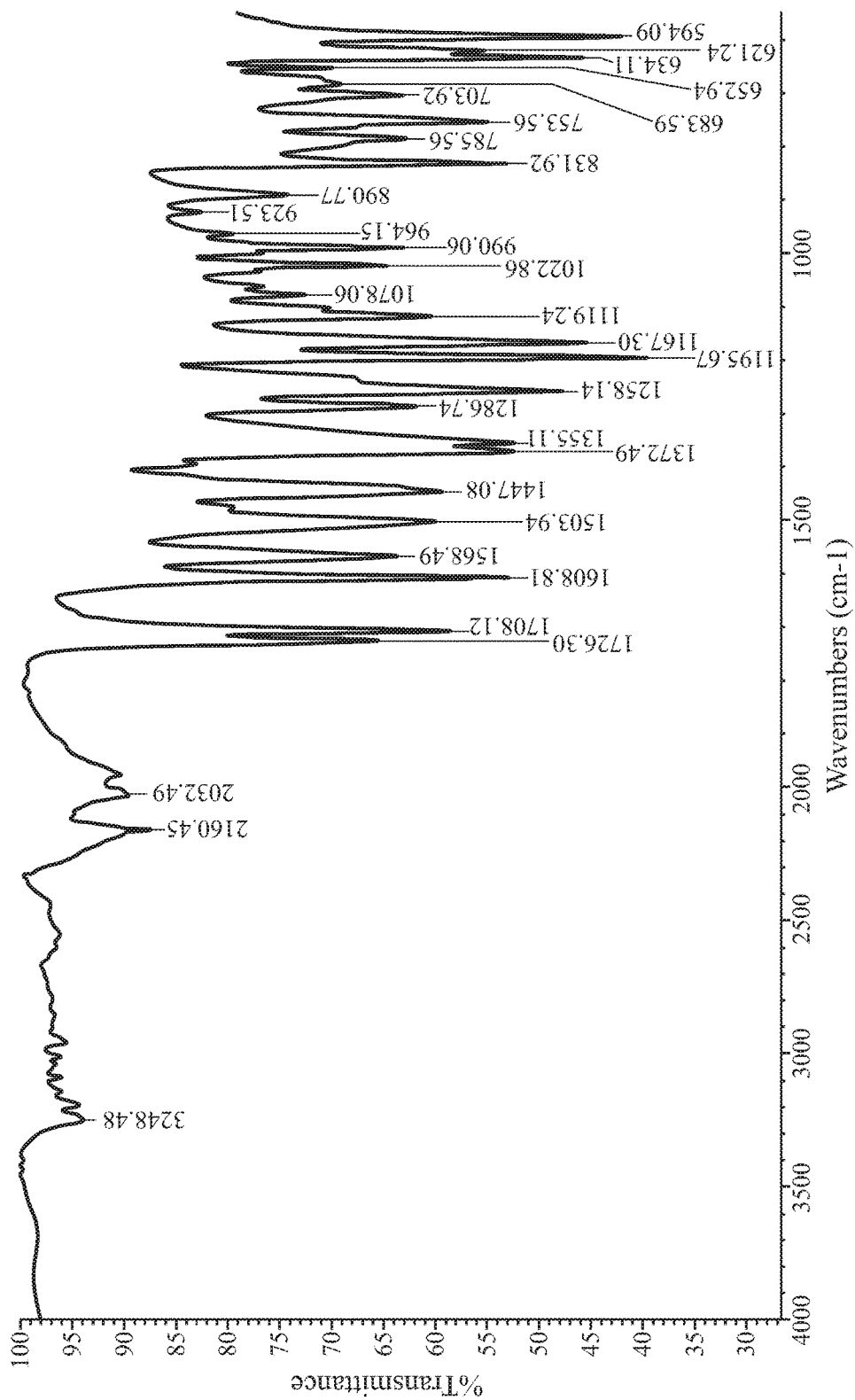
FIG. 1 is a graph showing the results of an infrared (IR) spectrograph of crystalline modification I of halosulfuron-methyl, according to an embodiment of the invention.

The crystalline modification I of halosulfuron-methyl may be further characterized by Infrared (IR) spectroscopy. The IR spectrum was measured with the resolution of 4 cm$^{-1}$ and with the number of scans of 16 for the purified sample. The IR spectrum of crystalline modification I of halosulfuron-methyl can be identified by its characteristic functional group vibrations (characteristic bands) at 3248.48, 2160.45, 2032.49, 1726.30, 1708.12 and 1608.81 cm$^{-1}$ as shown in FIG. 1.

All IR spectra were obtained using the following acquisition parameters:

| | |
|---|---|
| FT-IR spectrometer | Bruker Tensor 37 |
| Diamond ATR unit | from Specac |
| Wavelength range | 550-4000 cm$^{-1}$ |
| Resolution | 4 cm$^{-1}$ |
| Number of scans | 16 |

Figure 3:
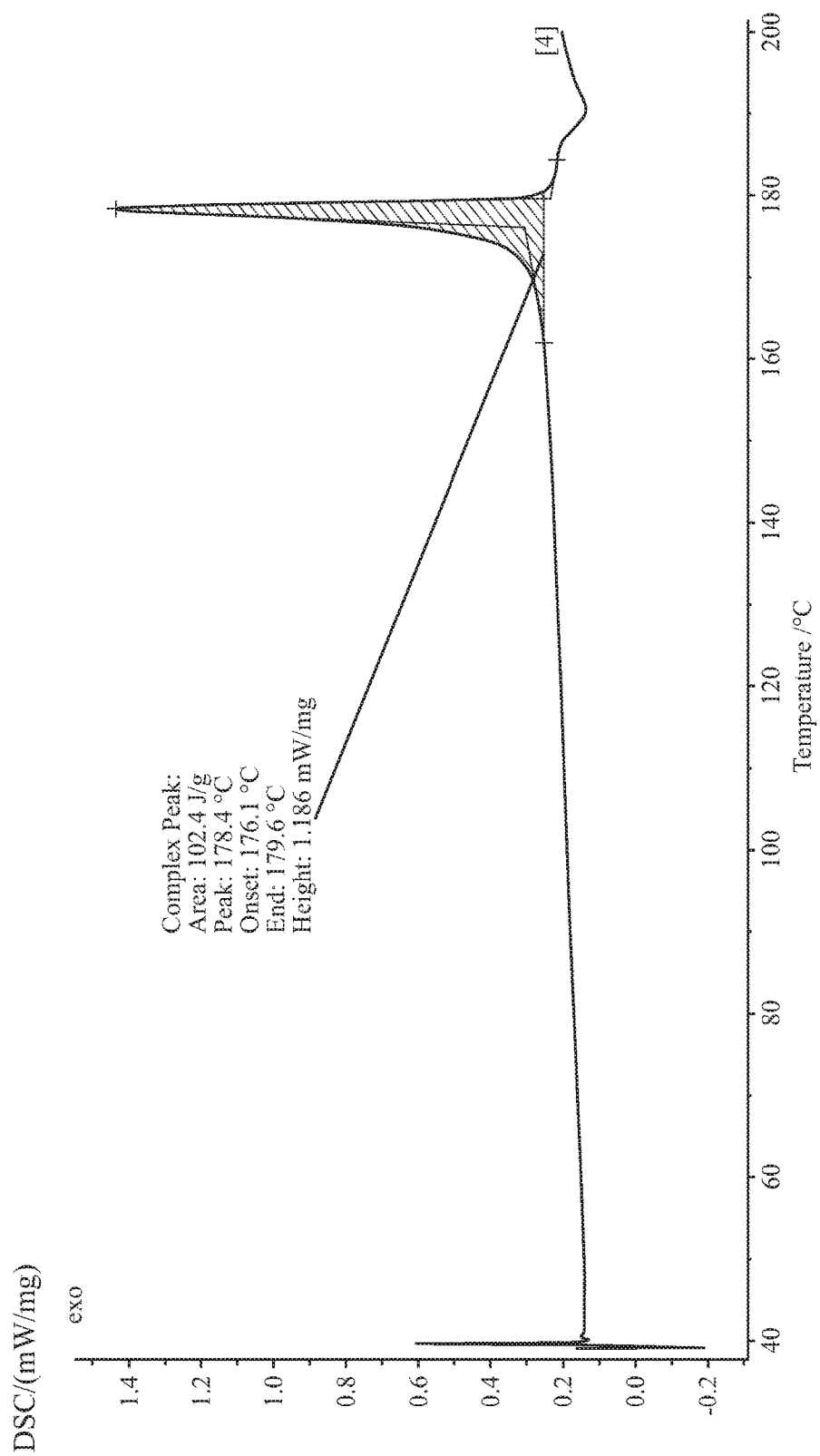
FIG. 3 is a Differential Scanning Calorimetry (DSC) thermogram of crystal modification I of halosulfuron-methyl, according to an embodiment of the invention.

The crystalline modification I of halosulfuron-methyl according to the invention may be further characterized by Differential Scanning Calorimetry (DSC) (FIG. 3). An endothermic peak with onset at about 176.1° C. and peak maximum at about 178.4° C. is shown in FIG. 3.

Methods for preparing amorphous halosulfuron-methyl are well known in the art.

Amorphous halosulfuron-methyl is manufactured and available on a commercial scale. A particularly suitable method for preparing amorphous halosulfuron-methyl is described in U.S. Pat. No. 4,668,277.

According to an embodiment of the invention, the crystalline modification I of halosulfuron-methyl can be obtained by the processes below:

Halosulfuron-methyl in amorphous state is dissolved and then crystallized from solvents.

In one aspect, the invention provides a process for preparing a crystalline modification I of halosulfuron-methyl comprising steps of:

i) dissolution of amorphous halosulfuron-methyl in at least one solvent;
ii) precipitation of the dissolved compound into crystalline modification I of halosulfuron-methyl of formula I; and
iii) isolation of the precipitated crystalline modification I.

Suitable solvents for preparing crystalline modification I of halosulfuron-methyl include halogenated hydrocarbons (for example, trifluoro methyl benzene, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyltetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, ethyl benzene, mesitylene), cymene, petroleum fractions within a boiling range of from 70° C. to 190° C., (cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), methyl ethyl ketone and aliphatic alcohols (for example, methanol, isopropyl alcohol, ethanol, n-propanol, isopropanol, n-butanol and tert-amyl alcohol).

Preferred solvents are nitrobenzene, toluene, xylene, benzene, chlorobenzene, dichlorobenzene, ethyl benzene, trifluoro methyl benzene, mesitylene, ether, methyl ethyl ketone.

In the present invention, it is preferred that the solvent comprises methyl ethyl ketone and/or xylene.

Hence, according to a preferred embodiment in step (i), amorphous halosulfuron-methyl is dissolved in a solvent comprising methyl ethyl ketone and/or xylene.

In a preferred embodiment of present invention, in step (i) of the process, amorphous halosulfuron-methyl is dissolved in a solvent or a solvent mixture as a concentrated solution by heating from room temperature or ambient temperature to reflux temperature or below the reflux temperature of the solvent or the solvent mixture. Preferably, the concentrated solutions can be prepared at the reflux temperature of the solvents. The concentration of the solution depends on the solubility of halosulfuron-methyl in the corresponding solvent or solvent mixture.

In step (ii) of the process, halosulfuron-methyl is crystallized from the solution. Techniques for effecting crystallization of halosulfuron-methyl from the solution are known to those skilled in the art. For example, in an embodiment, where the solution in step (i) is formed at elevated temperatures, crystallization may be effected by cooling the solution to room or ambient temperature or around 0° C. to 20° C. In one preferred embodiment, crystallization is effected by concentrating the solution formed in step (i) of the process.

Alternatively, or in addition thereto, seed crystals, in particular seed crystals of the aforementioned crystalline modification I of halosulfuron-methyl, may be added to the solution formed in step (i), to facilitate and/or enhance crystallization.

The seed crystal amount added to the concentrated solution is typically in the range of 0.001 to 10% by weight, preferably 0.001 to 2.5% by weight, often 0.005 to 0.5% by weight based on the weight of halosulfuron-methyl used for the preparation of concentrated solution in step (i). Preferably, the seed crystals are added to the concentrated solution at the temperature below the boiling point of the corresponding solvent or the solvent mixture.

Hence, the precipitation of the crystalline form I of halosulfuron-methyl can be effectively achieved from the concentrated solution by a person of ordinary skill in the art.

The precipitated crystalline modification I of halosulfuron-methyl obtained from step (ii) is isolated by the usual solid component separating techniques from solutions, such as filtration, centrifugation or decantation.

It is preferred that the solid precipitate of halosulfuron-methyl recovered during the crystallization stage is washed with a solvent one or more times. Preferably, the solvent employed in the washing stage consists of one or more components of the solvent employed for forming the solution in step (i), as described hereinbefore. Methyl ethyl ketone and xylene are particularly suitable solvent for washing the recovered solid of halosulfuron-methyl. The washing is usually carried out using the corresponding solvent or solvent mixture between room temperature and 0° C. depending on the solubility of the crystal in order to avoid the loss of crystal in the corresponding washing solvent as much as possible.

The invention also relates, in an embodiment, to a composition comprising the crystalline modification I of halosulfuron-methyl. The amount of the crystalline modification I of halosulfuron-methyl is less than 75% by weight of the composition, preferably less than 50% by weight of the composition, more preferably less than 30% by weight of the composition, still more preferably about 25% by weight of the composition.

The use of halosulfuron-methyl as a herbicide is known in the art and is used on a commercial scale. The crystalline modification I of halosulfuron-methyl is also active in controlling unwanted plant growth, such as weeds. Techniques of formulating and applying halosulfuron-methyl are known in the art, for example as disclosed in the prior art documents discussed hereinbefore. Halosulfuron-methyl in the crystalline modification I of the present invention may be formulated and applied in a manner analogous to those described for amorphous tribenuron-methyl.

Accordingly, in a further aspect, the invention provides a herbicidal composition comprising halosulfuron-methyl in the crystalline modification I as defined hereinbefore.

Accordingly, the invention furthermore provides processes for preparing compositions for controlling unwanted plant growth using the crystalline modification I of halosulfuron-methyl.

Accordingly, the invention furthermore provides a method for controlling unwanted plant growth, comprising applying to the plant, plant part, or surroundings of the plant, a herbicidally effective amount of crystalline modification I of halosulfuron-methyl.

The crystalline modification I of halosulfuron-methyl can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents, in a manner analogous to that known for amorphous tribenuron-methyl.

In this context, the crystalline modification I of halosulfuron-methyl may be present in a concentration of from about 0.1 to about 50% by weight of the total mixture, i.e., in amounts sufficient to achieve the required dosage. The formulations are prepared, for example, by extending the crystalline modification I of halosulfuron-methyl with water, solvents and carriers, using, if appropriate, emulsifiers and/or dispersants, and/or other auxiliaries.

These formulations are prepared by mixing the crystalline modification I of halosulfuron-methyl with customary additives, for example, surfactants, liquid diluents, solid diluents, wetting agents, dispersants, thickening agent, anti-foaming agent and other formulation ingredients.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such as methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide, and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates. Alkyl naphthalene sulphonates, sodium salts are particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenol-sulfonic acid; and naphthalene sulfonate-formaldehyde condensates. Of note are compositions comprising up to 10% by weight of dispersant. Ligninsulfonates such as sodium ligninsulfonates are particularly useful for the composition of the invention. Naphthalene sulfonate-formaldehyde condensates such as naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose. Synthetic thickeners include derivatives of the former categories, and also polyvinyl alcohols, polyacrylamides, polyvinylpyrrolidones, various polyethers, their copolymers as well as polyacrylic acids and their salts. Alkylpolyvinylpyrrolidones are particularly useful for the composition of the invention Other formulation ingredients can also be used in the present invention such as dyes, defoamers, drying agents, and the like. These ingredients are known to one skilled in the art.

The crystalline modification I of halosulfuron-methyl according to an embodiment of the invention can be present in formulations and in its use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as herbicide, the crystalline modification I of halosulfuron-methyl according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants, plant parts and their surroundings can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown, the place on which the plant propagation materials of the plants will be sown or the environment near the plants. The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment of the plants, plant parts and their surroundings with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the present invention are seen most when the herbicidal composition is applied to kill weeds in growing crops of useful plants: such as maize (corn) including field corns, pop corns and sweet corns, grain sorghum, sugarcane, cotton, wheat, rice, cereal, oats, potatoes, sugar beets, plantation crops (such as bananas, fruit trees, rubber trees, tree nurseries), vines, citrus, olive, amenity, asparagus, bushberries (such as blueberries), caneberries, cranberries, flax, okra, peppermint, rhubarb, spearmint, turf grass, grapevine and vegetable. In this invention, maize, sugarcane, rice, cereal, sweet corns, vegetable and turf grass are particularly beneficial.

All percentages are given in weight % unless otherwise indicated.

Embodiments of the present invention will now be described by way of the following examples, which are provided for illustrative purposes only, and not intended to limit the scope of the disclosure.

EXAMPLES

Example 1

Preparation of Amorphous Halosulfuron-Methyl in Accordance with the Disclosure of U.S. Pat. No. 4,668,277 with Modification in Example 1

Preparation of 3-chloro-4-methoxycarbonyl-1-methylpyrazole-5-sulfonamide isocyanate To a mixture of 7.0 g of 3-chloro-4-methoxycarbonyl-1-methylpyrazole-5-sulfonamide, 5.3 g of anhydrous potassium carbonate and 50 ml of dry acetone there was added 2.8 g of n-butyl isocyanate at room temperature, and the mixture was refluxed for 3 hours. After the reaction, acetone was evaporated under reduced pressure and the residue was dissolved in ice-water. After separation of a trace of water insolubles, the filtrate was made acidic with hydrochloric acid and the crystals formed were filtered, washed with water and dried to give 5.2 g of N-(n-butylcarbamoyl)-3-chloro-4-methoxycarbonyl-1-methlpyrazole-5-sulfonamide.

Into a mixture of 120 ml of dry toluene and the product obtained from the above procedure, 4.2 g of phosgene was passed under reflux. Then, the reaction mixture was further refluxed for 1.5 hours. After completion of the reaction, evaporation under reduced pressure to obtain crude 3-chloro-4-ethoxycarbonyl-1-methylpyrazole-5-sulfonyl isocyanate.

Preparation of halosufuron-methyl

The crude isocyanate was taken out in an amount of 0.98 g, and added into 20 mL of dry acetonitrile solution of 400 mg of 2-amino-4,6-dimethoxypyrimidine. The mixture was stirred at room temperature and the crystals precipitated were filtered, washed and dried to give 0.8 g of methyl 3-chloro-5-(4,6-dimethoxypyrimidin-2-ylcarbamoylsulfamoyl)-1-methylpyrazole-4-carboxylate.

Scheme 1. Synthesis of Halosulfuron-methyl

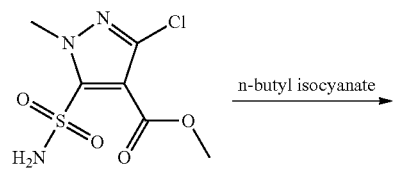

n-butyl isocyanate

-continued

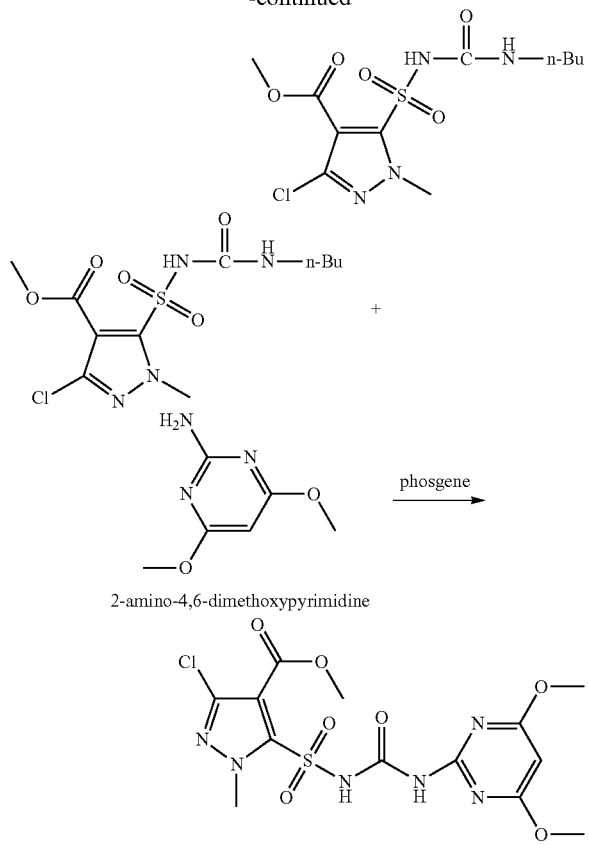

2-amino-4,6-dimethoxypyrimidine

Figure 4:
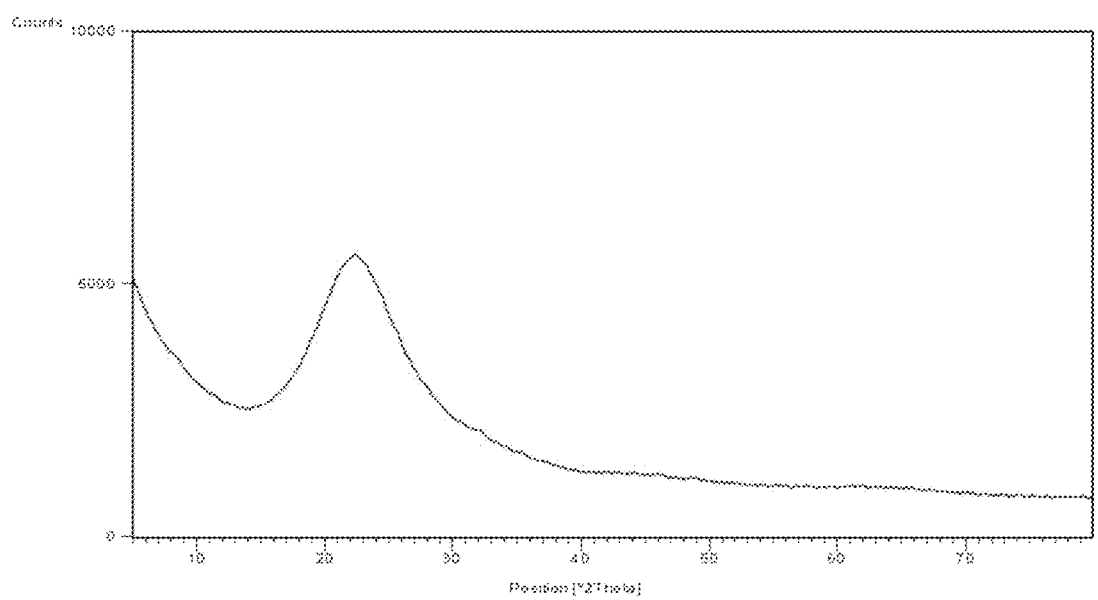
FIG. 4 is a graph showing the results of an X-ray powder diffractogram of amorphous halosulfuron-methyl.

As shown in FIG. 4, the X-ray powder diffraction pattern of the resulting halosulfuron-methyl product has no significant signals, which indicates the halosulfuron-methyl product prepared in accordance with the disclosure of U.S. Pat. No. 4,668,277 A1 is amorphous.

Preparation of Crystalline Modification I of Halosulfuron-Methyl

Example 2

Crystallization from Xylene

Halosulfuron-methyl sample prepared in Example 1 (10 g) was taken in a 3 neck round bottom flask along with xylene (60 mL) and the resulting slurry was heated to 90° C. to get a homogeneous solution. The insoluble particles, if any, were filtered and the solution was slowly cooled to room temperature. Upon cooling, fine crystals were formed and the heterogeneous mixture was stirred at room temperature for 2 h. Then, the slurry was filtered and washed with xylene (3 mL). The filtered crystals were dried under vacuum at 60° C. in order to remove the xylene traces from the crystalline product. The crystalline product thus obtained was having a purity of >98% and the recovered product as crystal was found to be not less than 80% yield.

The obtained crystal was analyzed by IR and X-ray powder diffraction and DSC, and found out to be crystalline modification I of halosulfuron-methyl as shown in FIGS. 1, 2 and 3, respectively.

Differential scanning calorimetry (DSC) (FIG. 3) shows an endothermic peak with onset at about 176.1° C. and peak maximum at about 178.4° C. as shown in FIG. 3.

IR spectrum of halosulfuron-methyl shows the functional group characteristic vibrations at 3248.48, 2160.45, 2032.49, 1726.30, 1708.12 and 1608.81 cm$^{-1}$ as shown in FIG. 1

X-ray powder diffractogram of crystals showed the reflexes as shown in FIG. 2 and the values are summarized in Table 1. The X-ray powder diffractogram was taken using a diffractometer in reflection geometry in the range from 3°–60° with increments of 0.03° using Cu-Ka radiation at 25° C.

Table 1. X-ray powder diffractogram reflexes of crystalline modification I of halosulfuron-methyl

TABLE 1

| crystalline modification I | |
|---|---|
| 2 θ (°) | d (Å) |
| 8.80 ± 0.2 | 10.05 ± 0.05 |
| 13.48 ± 0.2 | 6.60 ± 0.05 |
| 13.72 ± 0.2 | 6.46 ± 0.05 |
| 16.20 ± 0.2 | 5.47 ± 0.05 |
| 17.71 ± 0.2 | 5.01 ± 0.05 |
| 18.61 ± 0.2 | 4.77 ± 0.05 |
| 20.48 ± 0.2 | 4.34 ± 0.05 |
| 21.38 ± 0.2 | 4.16 ± 0.05 |
| 22.60 ± 0.2 | 3.93 ± 0.05 |
| 24.71 ± 0.2 | 3.60 ± 0.05 |
| 25.53 ± 0.2 | 3.49 ± 0.05 |
| 25.83 ± 0.2 | 3.45 ± 0.05 |
| 26.53 ± 0.2 | 3.36 ± 0.05 |
| 26.72 ± 0.2 | 3.34 ± 0.05 |

Example 3

Crystallization from Methyl Ethyl Ketone

Halosulfuron-methyl (5 g) sample prepared in Example 1 was taken in a 3 neck round bottom flask along with methyl ethyl ketone (35 mL) and the resulting slurry was heated to 70° C. to get a homogeneous solution. The resultant hot solution was filtered to remove the insoluble (if any) and the solution was slowly cooled to ambient temperature. Product was precipitated out as fine crystal during cooling and the mixture was stirred at room temperature for 2 h. Then, the slurry was filtered, washed with methyl ethyl ketone (3 mL). The filtered crystals were dried under vacuum at room temperature in order to remove the methyl ethyl ketone traces from the crystalline product. The crystalline product thus obtained was having a purity of >98% and the recovered yield was found to be not less than 80%.

The crystals were characterized as being halosulfuron-methyl crystalline modification I using IR spectrometry, X-ray diffraction and DSC, as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
| --- | --- | --- | --- |
| Halosulfuron-methyl, crystalline modification I, 98% (prepared in Example 2) | 40.8 | 0 | Active compound |
| Amorphous halosulfuron-methyl (prepared in Example 1) | 0 | 40.8 | Active compound |
| Sodium lignosulfonate (REAX ® 88B) | 22 | 22 | Dispersing agent |
| Alkylpolyvinylpyrrolidone | 20 | 20 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
| --- | --- | --- | --- |
| Halosulfuron-methyl crystalline modification I, 98% (prepared in Example 2) | 25.51 | 0 | Active compound |
| Amorphous Halosulfuron-methyl (prepared in Example 1) | 0 | 25.51 | Active compound |
| Lignosulfonic acid, sodium salt, (REAX ® 88B) | 15 | 15 | Dispersing agent |
| Naphthalenesulfonic acid, polymer with formaldehyde, sodium salt (TAMOL ® NN 8906) | 6 | 6 | Dispersing agent |
| Sodium acetate | 4 | 4 | Filler |
| Sodium carbonate | 4 | 4 | Filler |
| Non-ionic aqueous emulsion of Polydimethylsiloxanes | 1 | 1 | Antifoaming agent |
| Mannitol | Balance to 100% | Balance to 100% | Carrier |

Example 6

Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
| --- | --- | --- | --- |
| Halosulfuron-methyl, crystalline modification I, 98% (prepared in Example 2) | 25.51 | 0 | Active compound |
| Amorphous halosulfuron-methyl (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B | 15 | 15 | Dispersing agent |
| Naphthalenesulfonic acid, polymer with formaldehyde, sodium salt (TAMOL ® NN8906) | 6 | 6 | Dispersing agent |

TABLE 4-continued

| Ingredients | Weights % | | Function |
|---|---|---|---|
| Sucrose | 10 | 10 | Filler |
| Non-ionic aqueous emulsion of polydimethylsiloxanes | 1 | 1 | Antifoaming agent |
| Mannitol | Balance to 100% | Balance to 100% | Carrier |

Example 7

Determining Water Solubility

A stock pH 7 buffer solution was prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 time and up to about 5 times the amount of halosulfuron-methyl needed for saturation was added to a mixing vessel containing stock buffer solution at the test temperature (e.g., 20° C.). The mixture was magnetically stirred in the dark while being maintained at the test temperature. Samples were periodically removed for analysis. The samples were centrifuged using a high speed, temperature-controlled centrifuge at the test temperature for about 20 minutes at ≥12000 G to remove suspended particles. An aliquot of each supernatant was taken for analysis.

The concentration of halosulfuron-methyl in the supernatant was determined by a high pressure liquid chromatography (HPLC) with a reversed phase chromatography column and UV detection. The method should include development of best-fit calibration curves based on at least three standards using linear regression analysis. Samples were successively withdrawn from the mixing vessel and analyzed until three successive samples show little or no variation in concentration. The test is preferably replicated to ensure accuracy.

TABLE 5

| Sample | Formulation | Original concentration, % | Concentration measured by HPLC after treatment, % | Solubility |
|---|---|---|---|---|
| Halosulfuron-methyl, crystalline modification I, 98% (prepared in Example 2) | OD | 40 | 35 | 88% |
| Amorphous halosulfuron-methyl (prepared in Example 1) | OD | 40 | 14 | 35% |
| Halosulfuron-methyl, crystalline modification I, 98% (prepared in Example 2) | SG | 25 | 24.9 | 99.6% |
| Amorphous halosulfuron-methyl (prepared in Example 1) | SG | 25 | 15 | 60% |
| Halosulfuron-methyl, crystalline modification I, 98% (prepared in Example 2) | WG | 25 | 23 | 92% |
| Amorphous halosulfuron-methyl (prepared in Example 1) | WG | 25 | 12 | 48% |

Example 8

Cleanout Test

The test was conducted by dispersing in water a sample to produce a concentration that is normally used when applying the herbicide: 25% halosulfuron-methyl. The sample was added to tap water (300 mL) in a 400 mL beaker and magnetically stirred for 2 minutes. The mixture was then stirred for 2 minutes, whereupon the resulting dispersion was dispensed in three 100 mL aliquots to 4-oz (118 mL) polyethylene bottles. The bottles were capped, inverted twice and allowed to stand overnight.

After standing overnight, each individual bottle was inverted twice and the liquid contents were then poured out. Tap water (10 mL) was added and the bottle was inverted until all sediment was re-suspended, whereupon the contents were poured out. Tap water (100 mL) was added and the bottle was inverted twice and then allowed to stand undisturbed for 10 minutes. The bottle was inverted twice more and the contents were poured out. Acetonitrile (10 mL) was added to the bottle to extract any remaining material. The acetonitrile solution was analyzed by reversed-phase liquid chromatography with UV detection. The cleanout rating (the concentration of halosulfuron-methyl herbicide in the acetonitrile solution) is reported in % in Table 6 below. Lower cleanout ratings indicate more effective cleanout compared to higher ratings.

TABLE 6

| Sample | Formulation | Cleanout rating, % |
|---|---|---|
| Halosulfuron-methyl, crystalline modification I, 98% (prepared in Example 2) | OD | 5 |
| Amorphous halosulfuron-methyl, prepared in Example 1 | OD | 26 |
| Halosulfuron-methyl, crystalline modification I, 98% (prepared in Example 2) | SG | 0.1 |
| Amorphous halosulfuron-methyl, prepared in Example 1 | SG | 10 |

TABLE 6-continued

| Sample | Formulation | Cleanout rating, % |
|---|---|---|
| Halosulfuron-methyl, crystalline modification I, 98% (prepared in Example 2) | WG | 2 |
| Amorphous halo sulfuron-methyl (prepared in Example 1) | WG | 13 |

The invention claimed is:

1. A crystalline modification I of halosulfuron-methyl (methyl 3-chloro-5-(4,6-dimethoxypyrimidin-2-ylcarbamoylsulfamoyl)-1-methylpyrazole-4-carboxylate) exhibiting each of the following reflexes as 2θ values in X-ray powder diffractogram recorded using Cu—Kα radiation at 25° C.:

$2\theta = 8.80 \pm 0.2$ (1)

$2\theta = 13.48 \pm 0.2$ (2)

$2\theta = 13.72 \pm 0.2$ (3)

$2\theta = 16.20 \pm 0.2$ (4)

$2\theta = 17.71 \pm 0.2$ (5)

$2\theta = 18.61 \pm 0.2$ (6)

$2\theta = 20.48 \pm 0.2$ (7)

$2\theta = 21.38 \pm 0.2$ (8)

$2\theta = 22.60 \pm 0.2$ (9)

$2\theta = 24.71 \pm 0.2$ (10)

$2\theta = 25.53 \pm 0.2$ (11)

$2\theta = 25.83 \pm 0.2$ (12)

$2\theta = 26.53 \pm 0.2$ (13), and $2\theta = 26.72 \pm 0.2$ (14).

2. The crystalline modification I of halosulfuron-methyl according to claim 1, exhibiting an IR spectrum with the characteristic bands at 3248.48, 2160.45, 2032.49, 1726.30, 1708.12 and 1608.81 cm$^{-1}$.

3. The crystalline modification I of halosulfuron-methyl according to claim 1 exhibiting a Differential Scanning calorimeter (DSC) thermogram having an endothermic peak with onset at about 176.1° C. and peak maximum at about 178.4° C.

4. A process of preparing crystalline modification I of halosulfuron-methyl according to claim 1, comprising:

i) dissolution of amorphous halosulfuron-methyl in at least one solvent, ii) precipitation of the dissolved compound into the crystalline modification I of halosulfuron-methyl of formula I; and iii) isolation of the precipitated crystalline modification I.

5. The process according to claim 4, where the solvent is selected from the group consisting of xylene, and methyl ethyl ketone.

6. The process according to claim 5, wherein step ii) is effected by concentration of the solvent, or by cooling to ambient temperature or around 0 to 20° C., or by adding seed of the crystalline modification I, or any combination of these.

7. A crystalline modification I of halosulfuron-methyl obtained according to claim 4 and having a crystalline modification I of halosulfuron-methyl content of at least 98% by weight.

8. A composition comprising the crystalline modification I of halosulfuron-methyl according to claim 1 and at least one auxiliary.

9. The composition according to claim 6, wherein the auxiliary is selected from the group consisting of surfactant, a diluent, a wetting agent, a dispersant, a thickening agent, and an antifoaming agent.

10. The composition according to claim 6, in form of a suspension concentrate (SC), an oil-based suspension concentrate (OD), water-soluble granules (SG), a dispersible concentrate (DC), an emulsifiable concentrate (EC), an emulsion seed dressing, a suspension seed dressing, granules (GR), microgranules (MG), a suspoemulsion (SE) and water-dispersible granules (WG).

11. The composition according to claim 8, in form of in form of water-dispersible granules (WG) or water-soluble granules (SG).

12. A method for controlling unwanted plant growth, comprising applying to the plant, plant part, or surroundings of the plant, a herbicidally effective amount of crystalline modification I of halosulfuron-methyl according to claim 1.

* * * * *